United States Patent
Allen

(10) Patent No.: US 7,252,725 B2
(45) Date of Patent: Aug. 7, 2007

(54) ABSORBENT COMPOSITE PRODUCT AND PROCESS AND APPARATUS FOR MANUFACTURE THEREOF

(75) Inventor: Martin A Allen, Dawsonville, GA (US)

(73) Assignee: Nordson Corporation, Westlake, OH (US)

(*) Notice: Subject to any disclaimer, the term of this patent is extended or adjusted under 35 U.S.C. 154(b) by 659 days.

(21) Appl. No.: 10/238,000

(22) Filed: Sep. 9, 2002

(65) Prior Publication Data
US 2003/0018310 A1 Jan. 23, 2003

Related U.S. Application Data

(62) Division of application No. 09/470,354, filed on Dec. 22, 1999, now Pat. No. 6,502,615.

(51) Int. Cl.
  B32B 31/00 (2006.01)
  B32B 27/02 (2006.01)
  D04H 1/56 (2006.01)
  D04H 1/72 (2006.01)

(52) U.S. Cl. .............. 156/62.4; 156/167; 156/180; 156/181; 264/112; 264/113

(58) Field of Classification Search ............... 156/167, 156/180, 62.4, 181; 264/112–113
See application file for complete search history.

(56) References Cited

U.S. PATENT DOCUMENTS

| | | | | |
|---|---|---|---|---|
| 2,262,275 A | | 11/1941 | Fourness et al. ............ 270/41 |
| 4,668,566 A | * | 5/1987 | Braun ..................... 442/118 |
| 4,724,114 A | * | 2/1988 | McFarland et al. ........ 264/510 |
| 4,784,892 A | * | 11/1988 | Storey et al. .............. 428/172 |
| 4,818,597 A | | 4/1989 | DaPonte et al. ........... 428/284 |
| 4,995,928 A | * | 2/1991 | Sabee ...................... 156/164 |
| 5,455,110 A | | 10/1995 | Connor ..................... 428/903 |
| 5,458,592 A | * | 10/1995 | Abuto et al. .............. 604/378 |
| 5,470,639 A | | 11/1995 | Gessner et al. ........... 156/62.4 |
| 5,591,297 A | | 1/1997 | Ahr ......................... 156/521 |
| 5,707,468 A | | 1/1998 | Arnold et al. ............ 156/62.6 |
| 5,733,822 A | | 3/1998 | Gessner et al. ............. 442/35 |
| 5,762,844 A | | 6/1998 | Van Himbergen et al. .. 264/112 |
| 5,804,512 A | | 9/1998 | Lickfield et al. ........... 442/346 |
| 5,810,954 A | | 9/1998 | Jacobs et al. ............. 156/62.4 |
| 5,876,388 A | | 3/1999 | McDowall et al. ......... 604/384 |
| 5,928,209 A | | 7/1999 | Bodford et al. ............ 604/370 |
| 6,037,281 A | | 3/2000 | Mathis et al. .............. 442/394 |
| 6,114,596 A | | 9/2000 | Nayak et al. .............. 604/370 |
| 6,152,906 A | * | 11/2000 | Faulks et al. ......... 604/385.01 |
| 6,315,022 B1 | | 11/2001 | Herrin et al. ............. 156/457 |

FOREIGN PATENT DOCUMENTS

WO  WO 96/17569  6/1996

* cited by examiner

Primary Examiner—Sam Chuan Yao
(74) Attorney, Agent, or Firm—Wood, Herron & Evans, LLP

(57) ABSTRACT

A multi-layer absorbent product in a preferred embodiment includes a fibrous nonwoven top sheet, a fibrous nonwoven absorbent core layer, and a fibrous nonwoven substantially water-impervious back sheet. Each component layer or sheet is manufactured at a fiberizing station (i.e., melt spinning) and laminated together at a combining station. The preferred melt spinning apparatus is spunbond for the top sheet, meltblowing for the core layer, and a combination of spunbond and meltblowing for the bottom sheet.

31 Claims, 5 Drawing Sheets

ABSORBENT COMPOSITE PRODUCT AND PROCESS AND APPARATUS FOR MANUFACTURE THEREOF

This application is a divisional of application Ser. No. 09/470,354, filed Dec. 22, 1999 now U.S. Pat. No. 6,502,615, the disclosure of which is fully incorporated herein by reference.

FIELD OF THE INVENTION

The invention generally relates to equipment and processes for in-line manufacture of absorbent products. The equipment and the process utilize synthetic resins, such as thermoplastics, for the in-line manufacture of a multi-layer absorbent product. The invention also relates to a composite absorbent product comprising at least an impervious nonwoven bottom sheet, an absorbent nonwoven core, and a nonwoven top sheet.

BACKGROUND OF THE INVENTION

The equipment used for in-line manufacture of absorbent products, such as diapers, sanitary napkins, adult incontinent pads and the like, is generally referred to as converter equipment and the process is generally referred to as converting. The converter equipment processes separate rolls of stock material into the composite absorbent product. The converter equipment generally comprises stations for manufacturing the composite absorbent product as follows:
  (a) An absorbent core forming station comprising a hammermill is fed by pulp roll stock, such as cellulosic material with or without superabsorbent. The hammermill fiberizes the pulp, and a drum form or flat screen then forms the fiberized pulp. Alternatively, the absorbent core material can be supplied in roll form.
  (b) A top sheet station supplies a top sheet or coverstock layer comprising a nonwoven, such as spunbond polypropylene. The top sheet is unwound from a roll and applied to the core layer.
  (c) A bottom sheet station for supplying a liquid-impervious backsheet, such as polyethylene film, which is applied to the top sheet/core combination.

The absorbent product is a composite comprising a top sheet or cover stock, an intermediate core layer of absorbent material, and a bottom sheet or back sheet of impervious film. Most converter equipment includes devices for adding a variety of options, such as elastic waistbands and legbands, tab applicators, frontal tape applicators, transfer layers, and the like.

A characteristic common to all converter equipment and processes is that they use only roll stock to form the layers of the absorbent product. The roll stocks are separately manufactured into rolls, typically off site, and then transported to the site of use. These rolls are processed by the converter equipment to form multiple layer absorbent products.

Converter equipment typically comprises a large complex laminating machine which requires significant horizontal and vertical plant space. The complex equipment requires constant attention and fine tuning. Also, converter equipment generally produces a one-line output so the unit output is directly proportional to the line speed. Accordingly, the converter equipment must operate at extremely high speed, such as at line speeds of 700 to 1200 ft./min., to be economical.

As the converter equipment handles only preformed roll stock, it has a serious operational disadvantage. That is, once the multiple rolls are installed, the composition, properties or dimensions of the roll stocks cannot be changed. In order to produce two different types of absorbent products, or absorbent products with different properties, the converter must be shut down and a new roll or rolls substituted for the existing roll or rolls. For these reasons, it would be desirable to eliminate one or, preferably, more of the conventional roll stocks and form different layers of an absorbent composite product in-line.

SUMMARY OF THE INVENTION

The method and apparatus of the present invention most preferably involve fiberizing or melt spinning a synthetic resin, such as thermoplastic, at three separate stations. These three stations comprise a top sheet forming station, a core layer forming station, and a bottom sheet forming station.

The top sheet forming station includes at least one fiberizing die, such as a spunbond die, to form a nonwoven top sheet which is delivered in-line to a combining station. The bottom sheet forming station includes at least one spunbond die and, preferably, one or more additional meltblowing dies to form a water-impervious composite bottom sheet. The bottom sheet is preferably conveyed directly (in-line) to the core layer forming station where one or more meltblowing dies deposit a meltblown layer or a plurality of meltblown sublayers onto the bottom sheet to form a bottom sheet/core layer composite. The bottom sheet/core layer composite is conveyed in-line to the combining station where it is laminated with the top sheet to form an absorbent composite in accordance with the invention. In particular, the absorbent composite of this invention preferably comprises:
  (a) an inner top sheet of strong, fluid-permeable nonwoven;
  (b) a middle absorbent core layer of a nonwoven composed of hydrophilic microsized fibers, with preferably a sublayer of a coarser nonwoven in contact with the top sheet to aid in distributing liquid permeating the top sheet; and
  (c) a substantially fluid-impermeable back sheet of a strong nonwoven for containing the core layer and retaining fluid collected or absorbed therein.

Variations in the invention include using fiberizing dies at two stations, such as the top sheet and core layer forming stations, with roll stock used at the third station. Other variations of fiberizing dies and roll stock may be used as well. Also, the three layers may be affixed to one another, whether using fiberizing dies or roll stock, in various orders not withstanding that a preferred order of manufacture is specifically described herein.

The absorbent composite may be made an overall width transverse to the machine direction equal to multiple widths of each individual absorbent product. In such an embodiment, the composite width is slit longitudinally along the machine direction to form a plurality of slits, each slit being equal to the width of one absorbent product. The slits are then cut at longitudinal intervals to form individual absorbent products.

As described herein, the present invention contemplates several embodiments. Advantages and distinguishing features of some or all embodiments may be summarized as follows:
  (1) The absorbent composite comprises three or more layers or sheets of microsized fibers.

(2) Fiberizing or melt spinning of each component sheet or layer of the composite avoids the need for a converter. Thermoplastic resin is processed on site to form the compound sheets or layers and conveyed in-line to the combining station.

(3) The in-line manufacture of the component sheets or layers permits the rapid and easy change of materials (e.g., polymer grade), properties of the sheets or layers, and operating conditions.

(4) The manufacture of the large widths equal to several widths of individual absorbent products permits the line to operate at only a fraction of the speed of converters in achieving the same unit output.

Additional objectives, advantages and features of the invention will become more readily apparent to those of ordinary skill in the art upon review of the following detailed description of the preferred embodiments, taken in conjunction with the accompanying drawings.

BRIEF DESCRIPTION OF THE DRAWINGS

FIG. 7 is a top plan view, shown in schematic, illustrating a line for manufacturing disposable articles by longitudinally slitting the line output to form a plurality of parallel strips that are cross cut into individual articles.

DETAILED DESCRIPTION OF THE PREFERRED EMBODIMENTS

As mentioned above, the preparation of a composite absorbent comprises at least three main layers: (a) a top sheet, (b) an absorbent core layer, and (c) a substantially fluid-impervious bottom sheet. At least two of the layers are nonwovens prepared by extruding a thermoplastic polymer to form a nonwoven layer which is combined in-line with the other two layers. The term "in-line," as used herein, means the continuous laminating of an extruded nonwoven layer with another layer without the usual intermediate step of forming rolls of the nonwoven layer. It is preferred that at least two of the layers be formed by in-line extrusions. In the most preferred embodiment, all three layers are formed by in-line extrusion.

Figure 1:
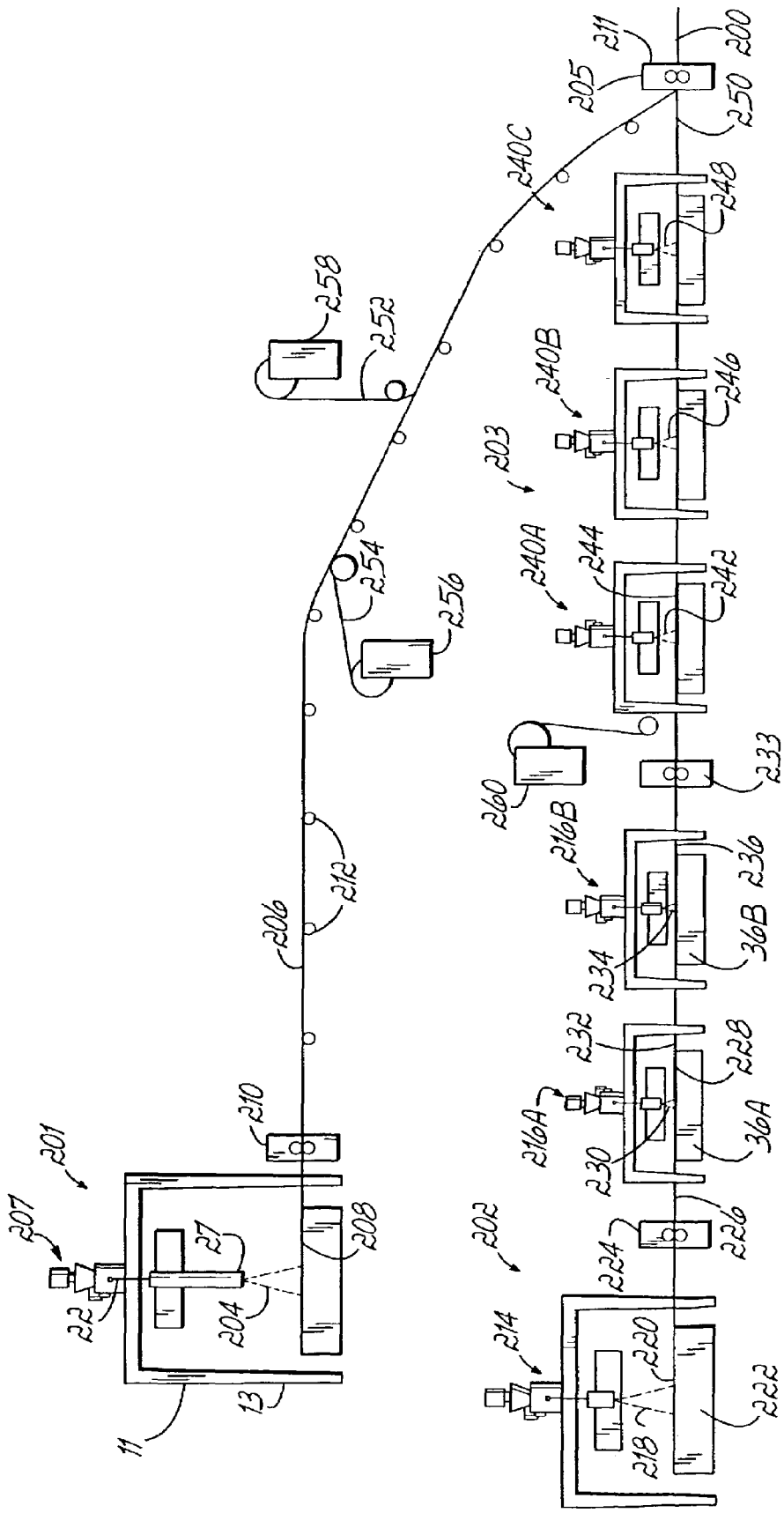
FIG. 1 is a side elevation schematic view of a line for fiberizing and laminating three nonwoven sheets or layers to form an absorbent composite.

FIG. 1 illustrates the most preferred embodiment as comprising three stations: a top sheet forming station 201, a bottom sheet forming station 202, and a core layer forming station 203. Nonwovens are formed at each station. The order of stations shown and described herein is preferred, but the order of operation may be changed as well.

The term "nonwoven" refers to a sheet, web or batt of directionally or randomly oriented fibers, made by bonding or entangling the fibers through mechanical, thermal, or chemical means. Nonwoven fabrics exclude paper and products which are woven, knitted, tufted, or felted by wet milling. The fibers are preferably man-made synthetics.

Although nonwovens may be made by a number of processes, the most popular processes—and those preferred for use in the present invention—are meltblowing and spunbond processes, both of which involve melt spinning of thermoplastic material. Meltblowing is a process for the manufacture of a nonwoven fabric wherein a molten thermoplastic is extruded from a die tip to form a row of fibers. The fibers exiting the die tip are contacted with converging sheets or jets of hot air to stretch or draw the fibers down to microsize diameter. The fibers are then deposited onto a collector in a random manner and form a nonwoven fabric.

The spunbond process involves the extrusion of continuous filaments through a spinneret. The extruded filaments are maintained apart and the desired orientation of the filaments is achieved by rotating the spinneret, by electrical charges, by controlled air streams, or by the speed of the collector. The filaments are collected on the collector and bonded by passing the layer of filaments through compacting roll and/or hot roll calendaring.

Spunbonded webs generally have large average diameter (e.g., 12-100 microns, typically 12-50 microns) which are heavier and stiffer than meltblown fibers. The meltblown fibers are generally smaller in average diameter (0.5 to 15 microns) than the spunbond fibers, but the meltblowing die assemblies can be operated to make much larger fibers.

A paper presented at "Fiber Producer Conference 1983," in Greenville, S.C., entitled "Nonwoven Fabrics: Spunbonded and Meltblown Processes" describes the two processes in detail. The disclosure of this paper are incorporated herein by reference. It should be noted that the terms "fibers" and "filaments" when used in connection with nonwovens and processes for manufacturing nonwovens are interchangeable.

The Absorbent Product

Figure 3:
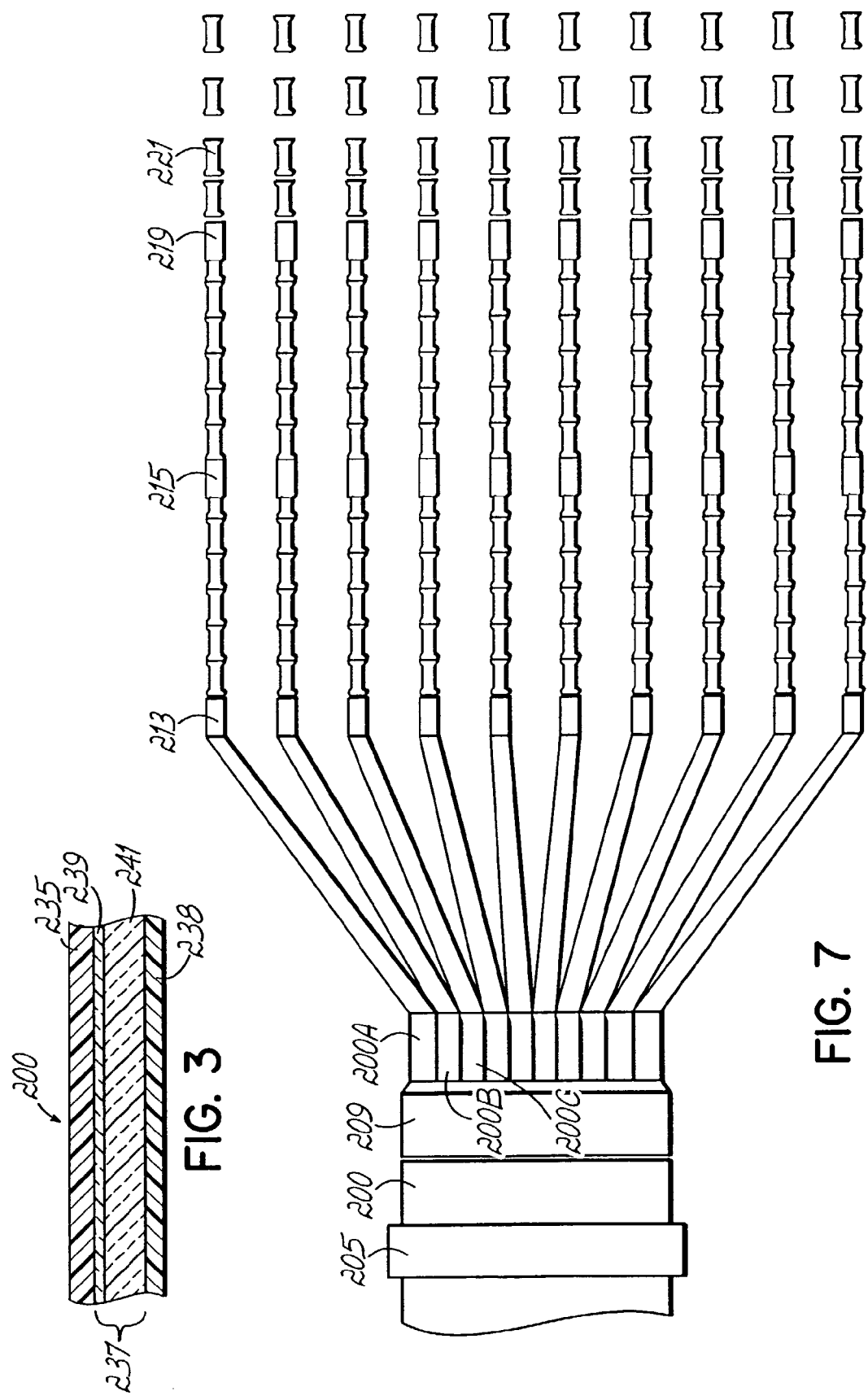
FIG. 3 is a cross-sectional view illustrating the three component layers of the disposable laminate.

The absorbent product of the present invention comprises at least three separate main layers that contribute separate properties and functions to the composite. As shown in FIG. 3, the absorbent product 200 comprises three main layers:

a top sheet 235, a core layer 237, and a bottom sheet 238.

The top sheet 235, sometimes referred to as cover sheet, covers the core layer 237 and contacts the wearer. It accordingly must exhibit comfort and be capable of transmitting fluid to the core layer 237. The top sheet preferably is made up of spunbound fabric, which exhibits a clothlike band and is fluid permeable. The fluid is generally a body fluid such as urine.

The core layer 237 is the absorbent layer and may comprise two sublayers, a thin acquisition and distribution layer 239 and a main absorbent layer 241. The core layer 237 preferably is made of a meltblown hydrophilic polymer which exhibits high absorbency. The difference between the distribution layer 239 and main absorbent layer 241 is one of degree, the former being made of coarser fibers (at least 5%, preferably 10%, and most preferably 25% coarser) than those of the latter to promote liquid distribution from the top sheet 235 to layer 241.

The bottom sheet 238, sometimes referred to as the back sheet, is a substantially liquid impervious sheet. This sheet generally is a thermoplastic film, but in accordance of a preferred embodiment of the present invention, is a combination of a spunbound layer and a meltblown layer, as described in detail below.

Each of the sheets or layers 235, 237, and 238 may be composed of a plurality of sublayers to impart or enhance the desired properties thereto.

The three distinct layers of the composite absorbent thus perform separate and diverse functions. When using conventional converters in accordance with the prior art, each layer, in roll stock, must be preselected, leaving no flexibility for altering the properties or dimensions of each selected layer. The in-line manufacture and lamination of layers in accordance with the present invention offers many significant advantages over the converter approach, but one advantage stands out; and that is the exceptional flexibility— within the limits of the equipment employed.

The Process and Apparatus

Figure 8:
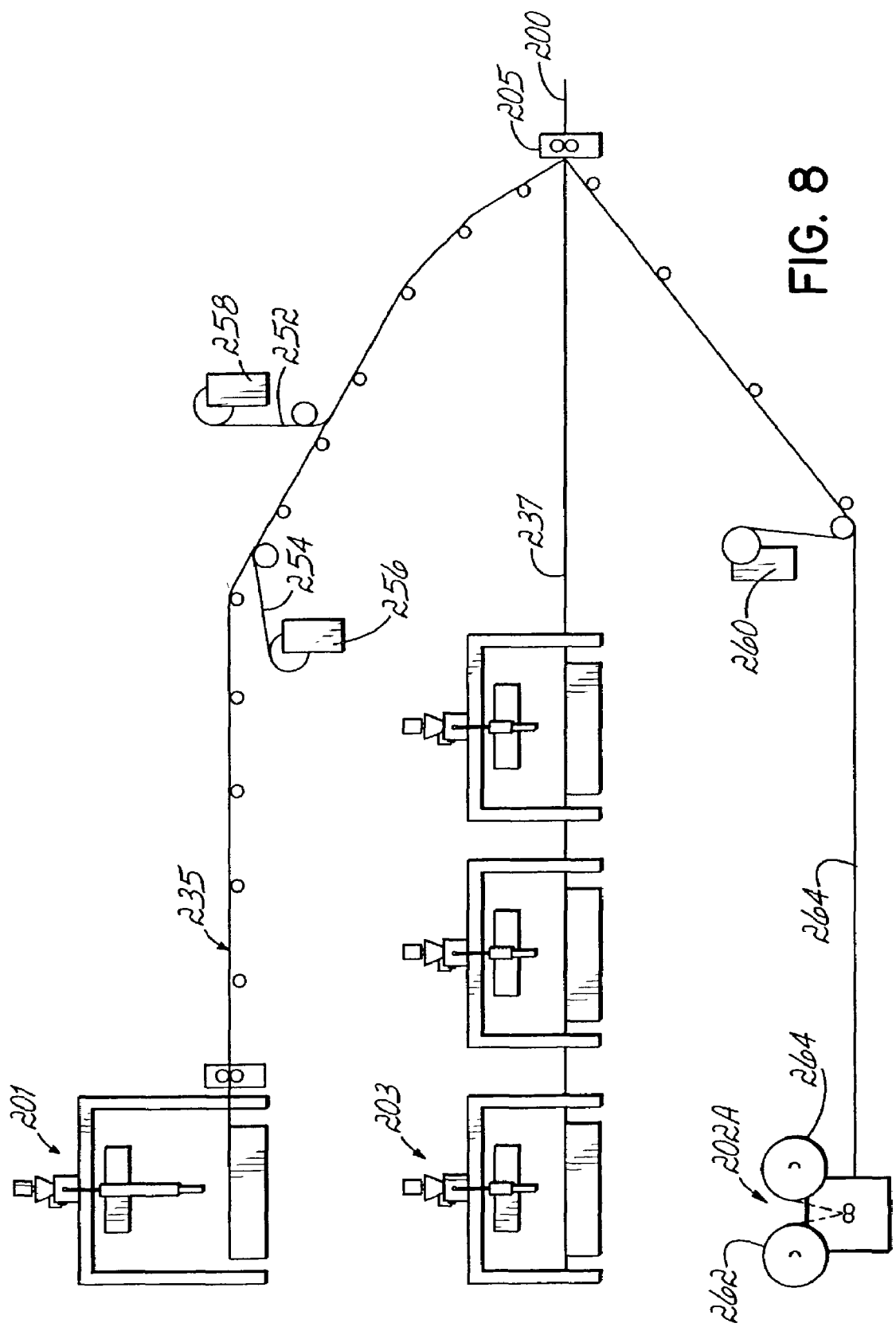
FIG. 8 is a schematic view similar to FIG. 1 illustrating another embodiment of the present invention.

The preferred process and apparatus of the present invention will be described with reference to FIG. 1, it being understood that other embodiments, such as that depicted in FIG. 8, are also contemplated.

With reference to FIG. 1, the in-line manufacture of an absorbent composite 200 comprises three main fiberizing stations: a top sheet forming station 201, a back sheet forming station 202, and a core forming station 203. As described in detail later, each station may include more than one fiberizing die for applying more than one layer at each station. (The term "fiberizing," as used herein, means the extrusion of a thermoplastic into filaments of fibers.)

Top Sheet Forming Station

The top sheet forming station 201 includes a die assembly 207 for extruding a plurality of synthetic fibers 204. The fibers are collected into a web 206 which, after further processing, is delivered, in an in-line fashion, to a layer combining station 205. Note that web 206 corresponds to top sheet 235, shown in FIG. 3. The top sheet 235 is the layer of the absorbent product that contacts the wearer, must be liquid permeable, and must possess a certain amount of integrity for assemblage and retention of the core layer. For this reason, the preferred top sheet 235 is a spunbonded web manufactured by a spunbond die. Although most spunbound dies may be used, the preferred top sheet forming station includes a die assembly 207 shown in FIG. 1 and described in more detail below.

A synthetic thermoplastic resin such as polypropylene is processed through the die assembly 207 into filaments 204 which are collected on a moving conveyor 208 (e.g., screen) as a loose web. The web is passed through a calendar 210 to bond the filaments together forming web 206. The web 206 is conveyed along rollers 212 to the combining station 205.

Any of the thermoplastic resins used in spunbond dies may be used to form layer 206. Polymers are copolymers of propylene and ethylene are preferred polymers with polypropylene being the most preferred.

Bottom Sheet Forming Station (202)

In order to provide the properties and strengths necessary for the bottom sheet 238 (i.e., back sheet), station 202 is preferably a combination of a spunbond die assembly 214 and at least one meltblowing die assembly. Preferably, station 202 uses two meltblowing die assemblies 216A and 216B. As schematically illustrated in FIG. 1, the spunbond die assembly 214 processes a thermoplastic resin such as polypropylene into filaments 218 which are collected as a web 220 onto a moving conveyor (e.g., a screen), described in more detail below with reference to FIG. 2. The web 220 is then passed through a calendar 224 to bond the filaments into a strong integrated web 226. Note that web 226 corresponds to backsheet layer 238 shown in FIG. 3. Since the back sheet 238 must be substantially liquid impermeable, the nonwoven web 226 should be treated to reduce its permeability. The terms "liquid impervious" and "liquid impermeable" are used interchangeably herein, meaning an aqueous liquid will not pass therethrough under conditions for use. This can be accomplished by spraying a sealant (e.g., an adhesive) onto a surface of the web 226, but preferably is achieved by meltblowing one or more layers of thermoplastic fibers onto the surface of web 226 by meltblowing die assemblies 216A and 216B.

As web 226 is conveyed under die assembly 216A by moving conveyor 228, or screen, meltblown fibers 230 are deposited thereon forming spunbond/meltblown composite 232. Continuous conveyance brings the two-layer composite 232 under the second meltblowing die 216B, where additional meltblowing of thermoplastic fibers 234 are sprayed onto the top surface of the spunbond/meltblown (SB/MB) composite 232 forming a three-layer SB/MB/MB composite 236.

The composite 236 is then passed through calendar 233 to thermobond the three layers together. In lieu of the calendar, adhesive may be used to bond the three layers together. Note that in this preferred embodiment, the SB/MB/MB composition 236 corresponds to backsheet 238 shown in FIG. 3.

The gradation of the fiber sizes in the back sheet results in a substantially liquid impermeable layer. The small-sized meltblown fibers combined with their strongly hydrophobic nature acts as a barrier for water. Moreover, the spunbond outer (exposed) layer gives the product a matte finish, strength, and a soft flexible hand. The liquid-impervious back sheet should be greater than 300 mm, as measured by RCST (raising column strike-through).

An important property of the back sheet 236 made at station 202 is that it is liquid (e.g., water) impermeable but air permeable (i.e., breathable). This not only provides comfort to the wearer, but has a manufacturing advantage. The air permeability permits meltblown layer or layers to be deposited thereon at station 203. In the meltblown process, the air/fiber mixture is delivered to a perforated conveyor such as a screen. The air passes the screen leaving the fibers accumulated in a randomly packed deposit on the screen. Back sheets such as film do not possess air permeability and therefore are not readily adapted for receiving meltblown fibers thereon.

Core Forming Station

The third fiberizing station 203 comprises one or more meltblown die assemblies. In FIG. 1, three meltblowing die assemblies 240A, 240B, and 240C are shown. The dies can be operated to (a) extrude identical fibers to form identical webs, (b) extrude different fibers using the same type of resin, or (c) extrude different fibers using different types of resin.

The back sheet 238 leaving station 202 is conveyed successively under the meltblowing die assemblies 240A, 240B, and 240C to receive a buildup of webs thereon. The back sheet 236, which can be a single web or a composite, is passed under the first die assembly 240A where thermoplastic fibers 242 are deposited thereon forming a composite 244. Composite 244 is then passed successively under die assemblies 240B and 240C where fibers 246 and 248 increase the thickness of the core layer. The final core layer made by station 203 comprises a stack-up of three sublayers. It is preferred that the web formed from fibers 248 on coarser (larger average fiber diameter) than the webs formed from fibers 242 and 246. The coarser fiber layer serves as a liquid acquisition and distribution layer for liquid permeating the top sheet as described below. The composite 250 exiting station 203 may be viewed as a composite of a back sheet 236 and a core layer 237, each of which may be made up of one or more sublayers as described above.

Combining Station

The top sheet 206 and core/bottom sheet composite 250 are brought together and passed through counter-rotating rollers 211 of the combining station 205. An adhesive may be applied to one of the confronting surfaces to add strength to the laminate.

The final product is a composite 200 (shown in FIG. 3) comprising a top sheet 235, a core layer 237, and a back sheet 238. As will be described in more detail below, the composite 200 is further processed through in-line stations to complete and package the absorbent products such as diapers.

In-Line Fiberizing Die Assemblies

Figure 2:
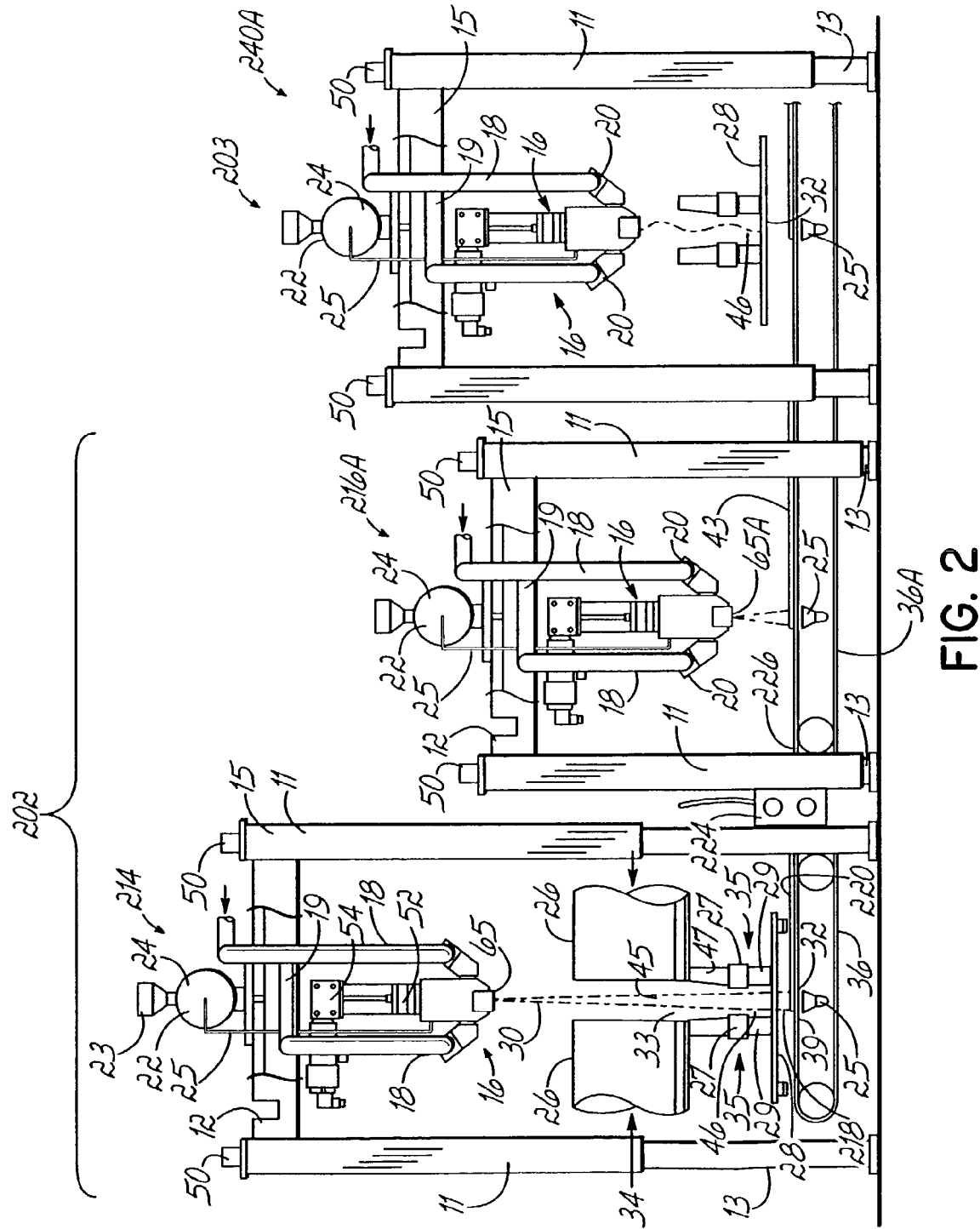
FIG. 2 is a side elevational of a line illustrating three extruders arranged in line for preparing a composite comprising three different types of nonwoven sheets or layers.

As noted above, the fiberizing die assemblies (e.g., meltblowing and spunbond dies) useable at the various stations according to the present invention can be any of a variety of commercially available designs. The preferred fiberizing die assemblies, however, are disclosed in FIG. 2 and described in detail in U.S. patent application Ser. No. 09/033,833, the disclosure of which is incorporated herein by reference. FIG. 2 illustrates the bottom sheet forming station 202 as comprising die assemblies 214 and 216A and core forming station 203 as comprising die assembly 240A in accordance with one embodiment of the invention. Note that the other die assemblies, 216B of station 202 and die assemblies 240B and 240C of station 203 (if used) can be identical respectively to die assemblies 216A and 240A described with reference to FIG. 2.

The fiberizing die assemblies 214, 216A, and 240A of the multi-station line may include many of the same components. Accordingly, the same reference numerals will designate the corresponding components of each die assembly. For example, the extruder at each die assembly 214, 216A or 240A, is designated by reference numeral 22.

Referring specifically to die assembly 214, this station comprises a support structure which may be in the form of four vertical legs 11 (two of which are shown in FIG. 2 and two being obscured) interconnected by cross beams 12. Each of the legs 11 are hollow and are concentrically mounted over internal legs 13 which are anchored to the floor. The legs 11 and 13 may be of any cross section but are preferably square and are sized to permit telescopic movement therebetween. The means for telescopically moving the outer legs 11 in relation to the inner legs 13 may take a variety of forms including hydraulic rams. The preferred height adjuster, however, is a conventional screw jack assembly 50 located at the upper end of each leg 11. The jack assembly 50 comprises a gear box driven by drive shaft which turns screw. Screw is threaded to bushing affixed to the upper end of leg 11. Turning the screw in one direction raises the legs 11 and support structure 15. The support structure 15 and equipment mounted thereon is thus moveable vertically between an upper position (die assembly 214) and a lower position (die assembly 216A).

A melt spinning assembly, shown generally as 16, is mounted on the moveable support structure 15 by air pipes which include a pair of vertical air pipes 18 and a horizontal pipe section 19. There are two pairs of air pipes 18, one pair being mounted on each side of the melt spinning assembly 16. One pair is connected to opposite ends of air box 20 (see FIG. 4) of the melt spinning assembly 16 as described below. The horizontal pipe 19 of each pair of pipes may be secured to cross beam 12. Thus, the melt spinning assembly 16 is suspended on the moveable support structure 15. The term "melt spinning assembly" is used herein in the generic sense for fiberization referring to both meltblowing and spunbond die assemblies. The melt spinning assembly 16 of die 214 includes spunbond die insert 65 shown in FIG. 6.

An extruder 22 mounted on the moveable support structure comprises hopper 23, barrel 24, and polymer feed line 25. The polymer feed line 25 delivers polymer melt to the melt spinning assembly 16 as described in more detail below.

Positioned directly under the melt spinning assembly 16 and in alignment therewith are a pair of air quench ducts 26 and a filament drawing device 27. These two components, 26 and 27, are both supported on a platform 28 in stacked relationship by brackets. The pair of ducts 26 define a quench zone 45 therebetween. The drawing device 27 is also constructed as a pair of conduits defining a filament drawing or stretching zone 46 therebetween. The vertical space between the quench ducts 26 and the drawing device 27 may include sheet metal housing 47 and the vertical space between drawing device 27 and platform 28 may include sheet metal housing 29. The platform 28 has an opening 32 formed therein. The filaments 30 discharging from the melt spinning assembly 16 descend through the quench zone 45, housing 47, draw zone 46, housing 29, opening 32, and are deposited as filaments 218 onto conveyor 36. The components 26, 27, 47, and 48 may be mounted on a wheeled carriage so that this assembly may be moved as a unit to the operating position or moved at right angles to the conveyor 36 to an offline position.

The conveyor 36 may traverse in underlying relationship all three assemblies 214, 216A, and 240A or, as illustrated in FIG. 2, may be in sections 36 and 36A to accommodate calendar 224. The collectors 36 and 36A are adapted to collect filaments from each die assembly. The conveyors 36 and 36A are each perforated or a fine-mesh screen to permit the passage of air therethrough. Vacuum means 25 positioned under conveyor 36 and 36A at each die assembly may be used to withdraw the air and debris.

Air is delivered to the quenching ducts 26 as shown schematically by arrows 34, and air is delivered to the filament drawing device 27 as shown by arrows 35.

The drawing device may be of any prior art construction including those described in U.S. Pat. Nos. 4,340,563 or 5,545,371, the disclosures of which are incorporated herein by reference. The spunbond filaments are stretched in the drawing device and laid down on collector 36 as web 220 which is passed through calendar 224 to form web 226.

Figure 4:
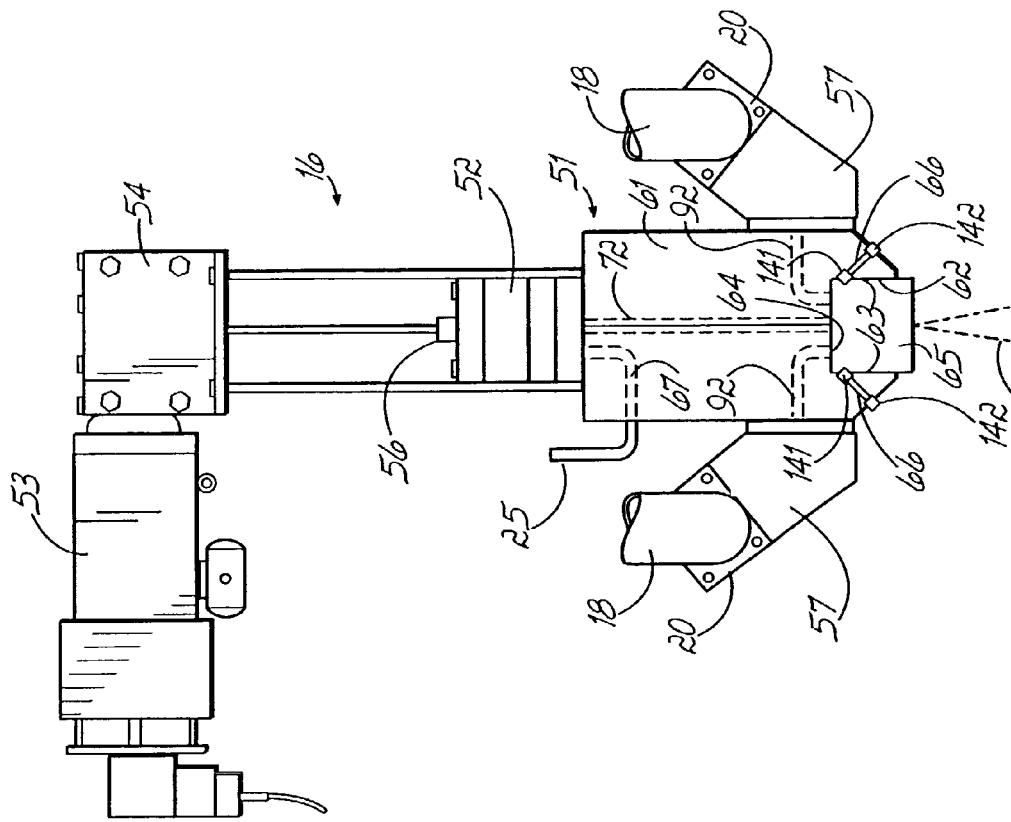
FIG. 4 is an enlarged front view of a meltspinning assembly shown in each of the extruders of FIG. 2.

The melt spinning assembly 16 shown in FIG. 4 comprises a die 51, positive displacement pump 52 such as a gear pump, motor 53, gear box 54, and shaft 56. The polymer feed line 25 delivers polymer melt to the spinning assembly 16. Motor 53 drives pump 52 which receives the polymer melt and delivers the same at metered rates to the die 51 which distributes and discharges the melt through orifices as filaments 30.

Figure 5:
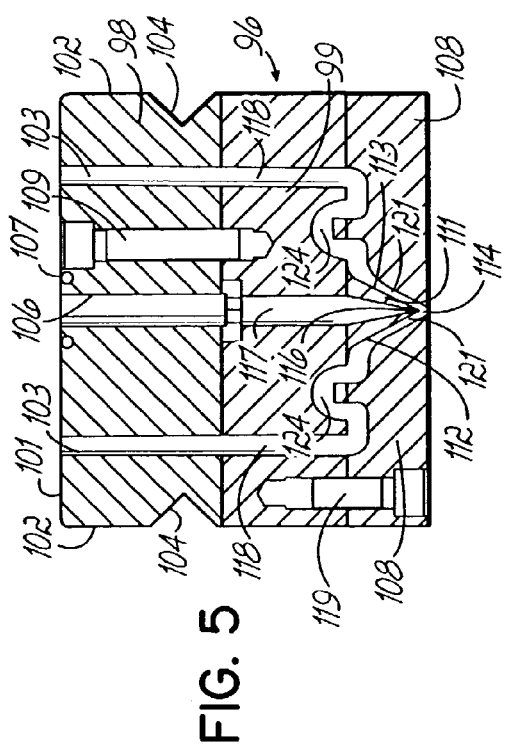
FIG. 5 is an enlarged view of a meltblowing insert useable in the assembly of FIG. 4.

Air connectors 57 and 58 mounted on each side of the die 51 connect to the air lines 18 which deliver pressurized hot air to the die 51 in its meltblowing mode (FIG. 5). The gear pump 52, motor 53, and gear box 54 may be similar to that described in U.S. Pat. No. 5,236,641, the disclosure of which is incorporated herein by reference. The die 51 comprises a die body 61 having a downwardly opening cavity 62 formed in its lower end. Die body 61 may be constructed in halves as illustrated in FIG. 4, wherein one half has an internal passage 67 connected to line 25 for feeding the polymer melt to the inlet of pump 52. The cavity 62 is defined by two elongate side walls 63 and top surface 64. Elongate, V-shaped grooves are formed on each side wall 63, as illustrated. The die body 61 has longitudinally spaced passages for interconnecting air connectors 57 with opposite sides of the cavity 62.

The die body 61 may have formed therein a conventional "coathanger" distribution passage for feeding a polymer melt to the die inserts described below. Electrical heaters may be mounted in the die block 61 for maintaining the temperature of the die body at the operating level. As mentioned previously, the air box 20 on each side of the die body 61 is suspended between pipes 18. Each air box 20 defines an internal elongate square chamber which extends substantially the entire length of the die body 61 and is connected to the air connector 57 through plate by welded connections. The connector 57 may be a welded assembly of plates which in combination define an internal air chamber and is bolted to each side of body 61 by bolts. Each connector 57 conducts air through passages 92 to the die inserts 65. The die insert assembly 65 which fits into and is mounted within cavity 62 may be in the form of a meltblowing die (herein referred to as meltblowing die insert) shown in FIG. 5 or may be in the form of a spunbond spinneret (herein referred to as a spunbond die insert) shown in FIG. 6.

Referring first to the embodiment using the meltblowing die insert 96, this assembly comprises a support member 98 and a die tip 99 mounted thereon. Members 98 and 99 are joined by a series of bolts (one shown as 109). Member 98 has a top surface 101 which contacts surface 64 of cavity 62, and has side walls 102 which fit in close conformity with the side walls 63 of cavity 62. Also formed in the support member 98 are a pair of longitudinally extending V-shaped grooves 104. These grooves align with the cavity grooves with the insert 96 mounted in cavity 62. A plurality of air holes 103 extend vertically through the support member 98. The inlet of each air passage 103 is aligned with the outlet 92 of each air passage formed in the die body 61. Also formed in the support member 98 is an elongate channel 106 that extends through the longitudinal axis thereof. The inlet of channel 106 registers with channel 72 of the die body with the meltblowing die insert 96 mounted in cavity 62. An O-ring 107 surrounds the inlet 106.

The die tip assembly 99 comprises a die tip 107 and a pair of air plates 108. The die tip 99 has a downwardly projecting triangular nosepiece 11 defined by converging surfaces 112 and 113. Surfaces 112 and 113 meet at apex 114, and a plurality of orifices 116 are spaced longitudinally along the apex 114. A polymer flow channel 117 extends through the die tip 99 and has an inlet which is aligned with polymer flow passage 106 of support member 98. The flow passage 117 pinches down to deliver polymer to the orifices 116. The nose piece 111 may be integrally formed in the die tip 99 as illustrated or it may be a separate piece bolted to the body of the die tip 99.

Also formed in the die tip 99 are air passages 118 which register with air passages 103 of support member 98. The air plates 108 are mounted on the die tip 99 by a plurality of bolts, one shown as 119. The air plates 108 flank the nosepiece 111 and define a converging gap 121 between confronting edges of the air plates 108 and surfaces 112 and 113. Each air plate 108 defines with a confronting surface of the die tip a tortuous air passage 124.

The meltblowing die tip insert 96 fits in close conformity in cavity 62 of the die body 61. The polymer flow passages and air passages of the assemblies are respectively in fluid communication so that air flows through the assembly and discharges as converging air sheets at the apex 114 of the nosepiece as polymer flows from the pump 52 through the die body 61, the meltblowing die insert 96 discharging as filaments through orifices 116 of the die tip.

Figure 6:
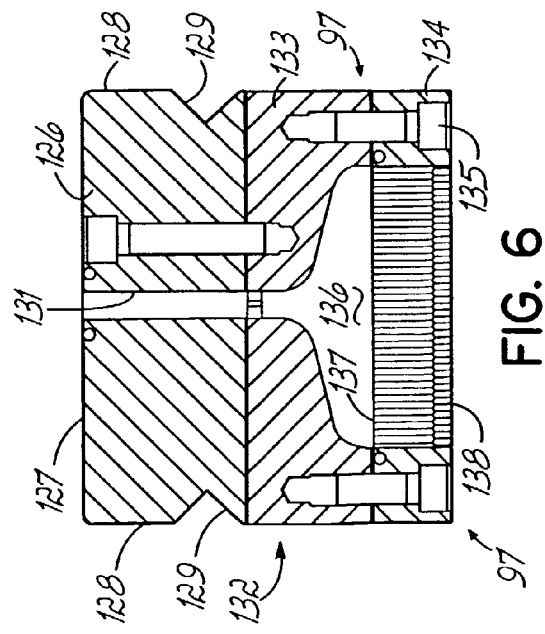
FIG. 6 is an enlarged view of a spunbond die insert useable in the assembly of FIG. 4.

The spunbond die insert 97, shown in FIG. 6, comprises a support member 126 which may be substantially identical to support member 98 described previously except no air passages are formed therein. The support member 126, however, does have the top surface 127, side surfaces 128, and V-shaped grooves 129 which may be identical surfaces 101, 102, and grooves 104, respectively of the meltblowing die insert 96. Support member 126 is provided with a polymer opening or channel 131 which aligns with channel 72 of the die body 61 with the die insert 97 mounted in cavity 62. Note that since there are no air passages in support member 126, the air passages 92 in the die body 61 are blocked off by surface 127.

The support member 126 is attached to spunbond spinneret 132 which comprises a body member 133 and a spinneret plate 134 bolted together by a plurality of bolts 135. The body member 133 in combination with the plate 134 defines a feed chamber 136 having an inlet in registry with passage 131 of the support member 128. The spinneret plate 134 includes a plurality of flow passages 137 formed therein which reduce down to orifices 138 at their outlets. The orifices 138 may be in accordance with well-known spunbond practices. (See for example U.S. Pat. Nos. 4,340, 563; 5,028,375 and 5,545,371).

Each of the die inserts 96 and 97 are selectively inserted into the cavity 62 of the die body 61 and maintained there in place by a pair of square bars 141 which fit into square holes defined by V-grooves 66 and 104 or 129 on each side wall of the cavity 62. With the selected die insert 96 or 97 in place and the bars 141 inserted, bolts 142 spaced along, and threaded thereto, each side of die body 61 engages one side of the bar 141 so that turning the bolts in one direction clamps the insert sealing onto top surface 64.

The above description of the die body 61 and meltblowing or spunbond die inserts 96 and 97 makes it clear that the system can be readily converted from one mode to the other by simply selecting the insert die and inserting it into the cavity 62. This, of course, requires the adjustment of the moveable support structure 15 to accommodate the operating mode. The means for inserting the die insert 96 or 97 into cavity 61 may be manual or automatic. Assembly 214 shown in FIG. 2 depicts the spunbond mode and assemblies 216A and 240A depict the meltblowing modes, where polymer melt is delivered from the extruder 22 through the melt spinning assembly 16 provided with meltblowing die insert 96 and discharged as microsized filaments from the row of orifices 116. The filaments are contacted on opposite sides by converging hot air streams and carried to and deposited on the conveyor 36A.

For the spunbond mode of operation (assembly 214), the spunbond die insert 97 is inserted in the die body 61. The moveable substructure 15 is moved to its upper position. The quench air assembly 26 and filament drawing device 27 are positioned in place by moving the carriage to the position shown in FIG. 2. Air is delivered to the quench ducts 26 and to the drawing device 27 while filaments 30 extruded through orifices 138 descend from the spinning assembly 16 through the quench zone 45 and drawing zone 46. The filaments 218 leaving the drawing device are deposited on the conveyor 36.

Fiberizing die assembly 216A is provided with a meltblowing die insert 65A. The other components including extruder 22, platform 12, telescopic supports 11, 13, polymer delivery line 25, piping 18, motor 53 and drive assembly 54, 56, and pump 52 may be same as those described for die assembly 214.

Fiberizing assembly 240A represents the core forming station 203, where in the assembly 240A, the melt spinning assembly 16 is provided with a meltblowing die insert 96 and is mounted above the drawing device 27. As illustrated, the device 27 may be mounted on the platform 28 which may be mounted on a carriage for removing or inserting the device 27 in the line. Sheet metal may be also used to define housings 38 and 39 through which the meltblown fibers must pass. As the fibers pass through housing 38, drawing zone 46 and housing 39, the downwardly converging sheets of air contact the meltblown filaments imparting drag forces to further drawdown the fibers. The additional drawdown by the use of the filament drawing device produces microsized fibers in the range of 0.5 to 5 microns, preferably 1 to 2 microns.

Note that in this alternative mode of meltblowing operation, the DCD (die to collector distance) is much larger than the DCD for conventional meltblowing as is apparent by comparing assemblies 216A and 240A. With the drawing device 27, the DCD ranges from 3 to 8 feet, preferably from 3 to 7 feet and most preferably 4 to 6 feet. The assembly 240A is adapted to produce a high loft web (e.g., basis weight between 5 and 500 GSM, preferably between 20 and 100 GSM). Additional die assemblies may be added at each station as desired, and as illustrated in FIG. 1. The fiberizing die assembly 207 for manufacturing the spunbond top sheet may be identical to assembly 214 shown in FIG. 2.

Operation

In operation, the top sheet 206 is made at station 201 by continuously fiberizing and calendaring a thermoplastic to form a web which is conveyed to the combining station 205. Optional components 252, 254, described in more detail below, may be prepared at stations 256 and 258 and attached to web 206 between stations 201 and 205.

Simultaneously, the bottom sheet 238 is made by fiberizing and calendaring a thermoplastic to form web 226, which is conveyed successively under meltblowing die assemblies 216A and 216B of station 202 where additional fiberized layers are superimposed on web 226. The composite exits station 202 through calendar 233 as bottom sheet 238 and is conveyed to the core forming station 203.

In station 203, one or more fiberization die assemblies (e.g., 240A, 240B, and 240C) arranged in series continuously deposit one or more layers or sublayers onto web 238. The nonwoven webs formed in station 203 are characterized as high loft absorbent webs.

The webs exit station 203 as composites 250, which for purposes of the present invention, comprise a core layer 237 overlying bottom sheet 238, even though each of these components 237 and 238 may consist of one or more sublayers bonded together by glue, entanglement or other methods. The core layer/bottom sheet composite 250 is combined with top sheet 235 in calendar 205 forming the composite 200. The component layers may be bonded together, for example, by adhesives or thermobonding. As described in more detail below, the width of composite in exiting calendar may range from just a few inches (e.g., 6") to several feet.

In a preferred embodiment, schematically depicted in FIG. 7, the composite web 200 exiting calendar 205 is several feet wide to allow for slitting the web 200 into a plurality of individual longitudinal strips 200A, 200B, 200C, etc., each strip being approximately the width of a single diaper. The slitting may be carried out by a conventional slitter indicated at 209.

The individual strips (200A, 200B, and 200C) are processed through conventional facilities which may include one or more of the following: (a) leg cutouts at station 213, (b) frontal tape attachment at station 215, fastener attachments at station 219, and cut off at longitudinal intervals at station 221. These steps may be performed by modules similar to that used in converters.

As schematically illustrated in FIG. 7, the composite web 200 exiting calendar 250 at slitter 209 is slit into individual strips 200A, 200B, 200C, etc. which are separated using rollers (not shown) and are in parallel and processed through the steps mentioned above.

A significant advantage of separating the composite web 200 into a plurality of strips (200A, 200B, etc.) vis-á-vis the converter approach is that the apparatus for carrying out the present invention can be operated at only a fraction of the line speed of the converter. Since the conventional converter processes only a single series of diapers, economics require faster and faster operation. For example, line speeds of state-of-the-art converters process from 400 to 800 diapers per minute. The apparatus for carrying out the preferred method of the present invention which simultaneously produces a number (n) of strips (200A, 200B, etc.) can be operated at a fraction (1/n) of the speed of converter and achieve the same diaper output. For example, the number of strips (200A, 200B, etc.) shown in FIG. 7 is ten. Therefore, this equipment can operate at 1/10 the speed of a single-line converter and achieve the same diaper output rate. Note also that the total width of composite 200 is equal to (n)(t) when n is the number of slits and t is the width of each slit. Preferably n ranges from 2 to 20 and t ranges from 2 inches to 20 inches.

The resin used in the spunbond die assembly 207 or 214 can be any of the commercially available spunbond grades, including a wide range of thermoplastic such as polyolefins, polyamides, polyesters, PVA, PVC, polyvinyl alcohol, cellulose acetate, elastomers such as Kraton™G, and the like. Polypropylene, because of its availability, is the preferred thermoplastic.

The resin used in the meltblowing dies may be any of the commercially available meltblowing grade thermoplastic resins. These include a wide range of polyolefins such as polylene and ethylene homopolymers and copolymers and elastomers such as Kraton™MG. Specific thermoplastics include ethylene acrylic copolymers, nylon, polyamides, polyesters, polystyrene, poly(methyl) methacrylate, polytrifluoro-chloroethylene, polyurethanes, polycarbonates, silicone sulfide, and poly(ethylene terephthalate), and blends of the above. The preferred resin is polypropylene. The above list is not intended to be limiting, as new and improved meltblowing thermoplastic resins continue to be developed.

The following are representative parameters of the preferred embodiment of the present invention:

|  | Broad Range | Preferred Range |
|---|---|---|
| Top Sheet Forming Station (201) | | |
| Die (length) (M) | 0.5 to 6 | 0.5 to 4.6 |
| Orifice | | |
| Diameter (inches) | 0.010 to 0.050 | 0.01 to 0.2 |
|  |  | (Typically 0.015) |
| Spacing (orifices/in) | 10 to 40 | 20 to 35 |
| Orifices | | |
| spacing (in) | 0.05 to 0.250 | 0.1 to 0.125 |
| diameter (in) | 0.001 to 0.040 | 0.016 to 0.020 |
| Quench Ducts | | |
| size height (m) | 0.5 to 2 | 0.8 to 1.2 |
| width (m) | 0.5 to 6 | 0.5 to 4.5 |
| Die to Collector | | |
| Distance (DCD) (inches) | 3 to 40 | 6 to 30 |
| Polymer Melt | | |
| Temp. (° F.) | 325 to 750 | 375 to 550 |
| Rate (Gr./hole/min) | 0.5 to 5 | 0.3 to 1.2 |
| Quench Air | | |
| Temp (° C.) | 2 to 20 | 5 to 15 |
| Rate (SCFM/in) | 1,000 to 20,000 | 5,000 to 15,000 |
| Drawing Device | | |
| Temp. | Ambient |  |
| Rate (SCFM/in) | 1 to 100 | 5 to 20 |
| Core Forming Station (203) | | |
| Meltblowing Dies | | |
| Number | 1 to 10 | 2 to 3 |
| Orifices | | |
| diameter (mm) | 0.1 to 1.0 | 0.3 to 0.4 |
| spacing (mm) | 0.05 to 1.0 | 0.1 to 0.3 |
| DCD (inches) | 3 to 20 | 3 to 8 |
| Polymer Melt | | |
| Temp. (° C.) | 175 to 300 | 200 to 270 |
| Rate (Gr./hole/min) | 0.1 to 5 | 0.2 to 1.2 |
| Primary Air | | |
| Temp. (° C.) | 175 to 300 | 200 to 275 |
| Rate (SCFM/in) | 2 to 100 | 5 to 30 |
| Bottom Sheet Forming Station (202) | | |
| Spunbond Dies* | | |
| Number | 1 or 2 | 1 |
| Meltblowing Dies | | |
| Number | 0 to 4 | 1 to 2 |
| Orifice diameter (mm) | 0.1 to 1.0 | 0.3 to 0.4 |
| Orifice spacing (mm) | 0.05 to 1.0 | 0.1 to 0.3 |
| DCD (inches) | 3 to 20 | 3 to 8 |
| Polymer | | |
| Temp (° C.) | 175 to 300 | 200 to 270 |
| Rate (Gr/hole/min) | 2 to 5 | 0.3 to 1.2 |
| Primary Air | | |
| Temp (° C.) | 175 to 300 | 200 to 275 |
| Rate (SCFM/in) | 2 to 100 | 5 to 30 |

*The length, orifice, quench ducts, collector specification and operating conditions may be the same as described for station 201.

Absorbent Composite

With reference to FIG. 3, the three-component composite 200 comprises top sheet 235, bottom sheet 238, core layer 237 including main absorbent layer 239 and acquisition/distribution layer 241. The properties and dimensions of the preferred component 200 may be as follows:

| Type of Web | Layers | Avg. Fiber Size (microns) | Basic Wt. (GSM) |
|---|---|---|---|
| Top sheet (235) | | | |
| Preferred: nonwoven | 1 | 12 to 100 | 4 to 40 |
| Most Preferred: spunbond | 1 | 12 to 50 | 4 to 40 |
| Core Layer (237) | | | |
| Layer 239 preferred | 1 | 5 to 100 | 2 to 100 |
| most preferred | 1 | 5 to 50 | 10 to 50 |
| Layer 241 preferred | 1 to 2 | 2 to 30 | 2 to 100 |
| most preferred | 1 to 2 | 1 to 15 | 10 to 50 |
| Bottom sheet (238) Spunbond | 1 | 12 to 100 | 2 to 100 |
| Meltblown | 1–2 | 1 to 15 | .5 to 20 |

The preferred absorbent composite should have a thickness between 10 mil to 500 inches, with the percentage proportion of each layer being as follows: top sheet 235, 1 to 10%; core layer 237, 25 to 75%; and bottom sheet, 1 to 10%. The preferred thickness of the product will be between 25 mil and 200 mil; the most preferred is between 25 and 100 mil.

Optional Equipment

Most diaper lines include facilities for applying optional diaper features, which include leg elastic, frontal tapes, waistbands, etc. These options can be applied in the conventional manner. FIG. 1 schematic illustrates leg applicator 260 as feeding thin elastic leg sections for attachment to bottom sheet 238. Waistband applicator 256, delivers waistbands 254 for attachment to the bottom surface of top sheet 206, and applicator 258 delivers leg cuffs (barriers) for attachment to the top surface of top sheet 206. Absorbent enhancing material such as superabsorbents may be added at strategic locations along the line.

Alternative Embodiment

It has been stated that at least two, and most preferably three, of the stations 201, 202, and 203, are in-line fiberizing stations. FIG. 8 illustrates a preferred embodiment comprising two fiberizing stations (e.g., 201 and 203), and a backsheet roll station 202A. The roll 262 may be any liquid-impervious sheet material but is preferably a plastic film such as polyethylene or polypropylene film.

In the FIG. 8 embodiment, the stations 201 and 203, respectively, form the top sheet 235 and core layer 237 as described previously and are conveyed to the combining station 205. Simultaneously, the film sheet 264 is unwound and delivered to the combining station 205 where all three layers are laminated together through calendar 205. A nonwoven layer unwound from station 202A may be combined with sheet 264, if desired.

While the present invention has been illustrated by a description of various embodiments and while these embodiments have been described in considerable detail, it is not the intention of the Applicant to restrict or in any way limit the scope of the appended claims to such detail. Additional advantages and modifications will readily appear to those skilled in the art. The invention in its broader aspects is therefore not limited to the specific details, representative apparatus and methods as shown and described. This has been a description of the present invention, along with the preferred methods of practicing the present invention as currently known. However, the invention itself should only be defined by the appended claims, wherein I claim:

The invention claimed is:
1. A method of manufacturing a composite absorbent article, the method comprising:
   (a) fiberizing a thermoplastic polymer to form a liquid-permeable nonwoven top sheet on a moving collector;
   (b) withdrawing the top sheet from the collector and delivering the same in-line to a combining station;
   (c) fiberizing a thermoplastic polymer at a bottom sheet forming station to form a nonwoven, substantially liquid-impervious nonwoven bottom sheet on a moving collector;
   (d) withdrawing the bottom sheet from the bottom sheet forming station and delivering the bottom sheet in-line to a core forming station;
   (e) fiberizing a thermoplastic polymer at the core forming station to deposit a nonwoven core layer on the bottom sheet delivered from the bottom sheet forming station to form a core layer/bottom sheet composite;
   (f) withdrawing the core layer/bottom sheet composite from the core forming station and delivering the same in-line to the combining station; and
   (g) laminating together the top sheet delivered from the top sheet forming station and the composite delivered from the core forming station to form a composite comprising a top sheet, a bottom sheet, and a core layer sandwiched therebetween.

2. The method of claim 1, wherein the fiberizing at the top sheet forming station is by a spunbond die to form a spunbond top sheet.

3. The method of claim 1, wherein the fiberizing at the bottom sheet forming station is by a spunbond die for forming a spunbond bottom sheet.

4. The method of claim 3, wherein the fiberizing at the bottom sheet forming station is by at least one spunbond die and at least one meltblowing die arranged in series to form a bottom sheet comprising a spunbond layer and a meltblown layer.

5. The method of claim 3, wherein the fiberizing at the core forming station is by at least one meltblowing die and wherein at least one meltblown layer is deposited on the bottom sheet.

6. The method of claim 5, wherein the core forming station comprises two or more meltblowing dies for depositing two or more meltblown layers in stacked relationship onto the bottom sheet.

7. The method of claim 1 and further comprising the step of withdrawing the three-layer composite from the combining station and passing the same through a cutting station wherein the composite is cut at longitudinal intervals to form a plurality of absorbent articles.

8. The method of claim 7, wherein prior to cutting the composite at longitudinal intervals, the composite is slit in the machine direction to form a plurality of longitudinal slits.

9. The method of claim 8, wherein the number of slits is n and the width of each slit is t, whereby the composite entering the cutting station has a width of nxt.

10. The method of claim 9, wherein n ranges from 2 to 20, and t ranges from 2 inches to 20 inches.

11. The method of claim 10, wherein n ranges from 5 to 15, and t ranges from 6 to 12 inches.

12. The method of claim 1, wherein step (a) forms a spunbond nonwoven.

13. The method of claim 1, wherein the thermoplastic polymer in all stations is a polymer or copolymer of propylene or ethylene.

14. The method of claim 1, wherein fiberizing at the core forming station forms a meltblown nonwoven having an average fiber size of between 0.5 to 100 microns.

15. The method of claim 14, wherein the thermoplastic polymer of step (c) is a polymer or copolymer of propylene or ethylene.

16. A method of manufacturing a three-layer composite absorbent, comprising the steps of:
   (a) continuously forming a liquid-permeable nonwoven top sheet layer by (i) extruding a thermoplastic polymer into fibers and (ii) collecting the fibers on a moving collector to form the liquid-permeable nonwoven top sheet thereon;
   (b) continuously forming a nonwoven absorbent core layer by (i) extruding a thermoplastic polymer to form fibers, and (ii) collecting the fibers on a moving collector to form the nonwoven absorbent core layer thereon;
   (c) continuously withdrawing the top sheet and the core layer from their respective collectors; and
   (d) continuously laminating the top sheet and the core layer withdrawn in step (c) with a substantially liquid-impervious bottom sheet to form a three-layer composite.

17. The method of claim 16, wherein the bottom sheet is a film of a synthetic polymer.

18. The method of claim 16, wherein the bottom sheet is a nonwoven liquid impermeable, air permeable layer.

19. The method of claim 16, wherein the bottom sheet is formed by (i) extruding a thermoplastic polymer to form fibers and (ii) collecting the fibers on a moveable collector.

20. The method of claim 19, wherein the fibers of the core layer are deposited directly onto the bottom sheet.

21. A method of manufacturing a diaper comprising:
   (a) fiberizing a thermoplastic polymer at a top sheet forming station to form a liquid-permeable nonwoven top sheet on a moving collector;
   (b) withdrawing the top sheet from the collector and delivering the top sheet in-line to a combining station;
   (c) fiberizing a thermoplastic polymer at a bottom sheet forming station to form a nonwoven, substantially liquid-impervious bottom sheet on a moving collector;
   (d) withdrawing the bottom sheet from the bottom sheet forming station and delivering the bottom sheet in-line to the combining station;
   (e) fiberizing a thermoplastic polymer into a core layer comprising a plurality of sublayers, the first sublayer being a fluid acquisition and distribution layer comprised of a first group of fibers and the second sublayer being a main absorbent layer comprised of a second group of fibers, the fibers of the first group being coarser than the fibers of the second group;
   (f) delivering the core layer to the combining station; and
   (g) combining the top sheet, bottom sheet, and core layer into a composite at the combining station.

22. A method of manufacturing in-line a composite absorbent article, the method comprising:
   continuously fiberizing a thermoplastic polymer at a top sheet forming station to form a liquid-permeable nonwoven top sheet on a moving collector;
   delivering the top sheet in-line to a combining station;

continuously fiberizing a thermoplastic polymer at a bottom sheet forming station to form a nonwoven, substantially liquid-impervious bottom sheet on a moving collector;

delivering the bottom sheet in-line to the combining station;

fiberizing a thermoplastic polymer at a core forming station to form a nonwoven core layer;

delivering the core layer in-line to the combining station; and laminating together the top sheet delivered from the top sheet forming station and the core layer delivered from the core forming station and the bottom sheet delivered from the bottom sheet forming station to form a composite absorbent article comprising a top sheet, a bottom sheet and a core layer sandwiched therebetween.

23. The method of claim 22 wherein the step of delivering the bottom sheet in-line to the combining station includes first delivering the bottom sheet in-line to the core forming station;

the step of fiberizing a nonwoven core layer includes forming the core layer on the bottom sheet delivered from the bottom sheet forming station to form a core layer/bottom sheet composite;

the step of delivering the core layer in-line to the combining station includes delivering the core layer/bottom sheet composite in-line to the combining station; and the step of laminating includes laminating together the top sheet delivered in-line from the top sheet forming station and the core layer/bottom sheet composite delivered in-line from the core forming station to form the composite absorbent article comprising a top sheet, a bottom sheet and a core layer sandwiched therebetween.

24. The method of claim 23, wherein the fiberizing at the top sheet forming station is by a spunbond die to form a spunbond top sheet.

25. The method of claim 24, wherein the fiberizing at the bottom sheet forming station is by a spunbond die to form a spunbond bottom sheet.

26. The method of claim 24, wherein the fiberizing at the bottom sheet forming station is by at least one spunbond die and at least one meltblowing die arranged in series to form a bottom sheet comprising a spunbond layer and a meltblown layer.

27. The method of claim 25, wherein the fiberizing at the core forming station is by at least one meltblowing die to form at least one meltblown core layer on the bottom sheet.

28. The method of claim 27, further comprising:
adding absorbent enhancing material to the core layer.

29. The method of claim 25, wherein the fiberizing at the core forming station is by two or more meltblowing dies to form two or more meltblown core layers in stacked relationship on the bottom sheet.

30. The method of claim 29, wherein the first meltblown core layer is a fluid acquisition and distribution layer and the second meltblown core layer is an absorbent layer; the first meltblown core layer is coarser than the second meltblown core layer.

31. The method of claim 27, further comprising:
withdrawing the composite from the combining station, slitting the composite in the machine direction to form a plurality of longitudinal slits, and cutting the longitudinal slits at intervals to form a plurality of composite absorbent articles.

* * * * *